United States Patent
Heigl et al.

(10) Patent No.: US 10,231,759 B2
(45) Date of Patent: Mar. 19, 2019

(54) BONE CLAMP

(71) Applicant: Brainlab AG, Munich (DE)

(72) Inventors: Rupert Heigl, Markt Schwaben (DE); Franz Fasel, Munich (DE); Andrew Ayala, Munich (DE)

(73) Assignee: Brainlab AG, Munich (DE)

( * ) Notice: Subject to any disclaimer, the term of this patent is extended or adjusted under 35 U.S.C. 154(b) by 67 days.

(21) Appl. No.: 15/522,685

(22) PCT Filed: Sep. 19, 2016

(86) PCT No.: PCT/EP2016/072197
§ 371 (c)(1),
(2) Date: Apr. 27, 2017

(87) PCT Pub. No.: WO2017/157485
PCT Pub. Date: Sep. 21, 2017

(65) Prior Publication Data
US 2018/0092667 A1    Apr. 5, 2018

(30) Foreign Application Priority Data

Mar. 17, 2016 (WO) .................. PCT/EP2016/055757

(51) Int. Cl.
*A61B 17/70* (2006.01)
*A61B 17/88* (2006.01)
(Continued)

(52) U.S. Cl.
CPC ...... *A61B 17/7047* (2013.01); *A61B 17/2833* (2013.01); *A61B 17/68* (2013.01);
(Continued)

(58) Field of Classification Search
CPC ............ A61B 17/6466; A61B 17/8866; A61B 17/7047
See application file for complete search history.

(56) References Cited

U.S. PATENT DOCUMENTS 2,777,347 A    1/1957  Sendoykas
3,750,652 A *  8/1973  Sherwin ............... A61B 17/025
                                                   600/217
(Continued)

FOREIGN PATENT DOCUMENTS

EP    1044653 A2   10/2000
EP    1884317 B1    2/2008
(Continued)

OTHER PUBLICATIONS

European Patent Office, International Search Report and Written Opinion for corresponding PCT/EP2016/072197 dated Dec. 20, 2016. pp. 1-11.

(Continued)

*Primary Examiner* — Nicholas J Plionis
(74) *Attorney, Agent, or Firm* — Tucker Ellis LLP (57) ABSTRACT

A bone clamp for attachment to a bone includes a first lever and a second lever that are connected to each other by a connection, a sliding block, and a screw. The first lever has a first lever arm and a second lever arm, and the second lever has a third lever arm and a fourth lever arm, the second ends of which are configured to contact the bone. The sliding block is slidably attached to the first lever arm, the screw is pivotably mounted in the sliding block, the first lever arm includes a threaded surface for engaging with the screw mounted in the sliding block, and the sliding block includes a sliding surface on which the third lever arm slides such that the second ends of the levers approach each other when the sliding block moves along the first lever arm.

20 Claims, 3 Drawing Sheets

(51) Int. Cl.
  *A61B 17/28* (2006.01)
  *A61B 17/68* (2006.01)
  *A61B 90/00* (2016.01)
  *A61B 17/00* (2006.01)
  *A61B 17/64* (2006.01)

(52) U.S. Cl.
  CPC .......... *A61B 17/8866* (2013.01); *A61B 90/39* (2016.02); *A61B 17/64* (2013.01); *A61B 2017/00407* (2013.01); *A61B 2090/3916* (2016.02); *A61B 2090/3983* (2016.02)

(56) References Cited

U.S. PATENT DOCUMENTS

| | | | |
|---|---|---|---|
| 4,187,840 A * | 2/1980 | Watanabe | A61B 17/808 606/86 R |
| 4,475,544 A | 10/1984 | Reis | |
| 4,944,739 A | 7/1990 | Torre | |
| 5,267,999 A | 12/1993 | Olerud | |
| 6,856,828 B2 * | 2/2005 | Cossette | A61B 90/39 600/429 |
| 7,341,594 B2 * | 3/2008 | Shluzas | A61B 17/7079 606/105 |
| 7,883,522 B2 * | 2/2011 | Hamada | A61B 17/02 604/164.01 |
| 8,007,435 B2 * | 8/2011 | Hartnick | A61B 17/0206 128/200.26 |
| 8,939,995 B2 | 1/2015 | Lechner et al. | |
| 2001/0053911 A1 | 12/2001 | Hehli et al. | |
| 2005/0277832 A1 | 12/2005 | Foley et al. | |
| 2009/0024127 A1 * | 1/2009 | Lechner | A61L 31/126 606/53 |
| 2011/0106183 A1 * | 5/2011 | Dell'oca | A61B 17/282 606/86 B |
| 2011/0118750 A1 | 5/2011 | Wu et al. | |
| 2012/0221059 A1 | 8/2012 | Mollman et al. | |
| 2015/0031985 A1 | 1/2015 | Reddy et al. | |

FOREIGN PATENT DOCUMENTS

| | | |
|---|---|---|
| GB | 249022 A | 10/2012 |
| WO | 2004/026155 A1 | 4/2004 |
| WO | 2013191819 A1 | 12/2013 |
| WO | 2016/044934 A1 | 3/2016 |

OTHER PUBLICATIONS

Wabeco-Remscheid, Maschinenschraubstock 100 mm-Schraubstöcke + Spannmittel, Product Catalog, https://lwww.wabeco-remscheid.de/catalog/productlview/id/4959/s/maschinenschraubstock-100-mm/category/209/ Apr. 26, 2017, pp. 1-2, Germany.

Ganter-Griff, GN 6303.1 Quick release knurled nuts, Steel | Otto Ganter, Product Catalog, https:f/www.ganter-griff.de/en/products/2.2-Tensioning-clamping-with-handles/GN-6303.1-Quick-release-knurled-nuts-Steel, Apr. 26, 2017, pp. 1-2, Germany.

European Patent Office, International Search Report corresponding to PCT/EP2016/055757, dated Jul. 12, 2016, pp. 1-6.

* cited by examiner

BONE CLAMP

RELATED APPLICATION DATA

This application is a national phase application of International Application No. PCT/EP2016/072197 filed on Sep. 19, 2016, which claims priority to PCT/EP2016/055757 filed on Mar. 17, 2016, which are hereby incorporated herein by reference.

TECHNICAL FIELD

The present invention relates to a bone clamp for being attached to a bone, for example for connecting a marker device to the bone.

SUMMARY

Many medical interventions require bone clamps, for example for attaching an object like a marker device to a bone. A bone clamp typically comprises two levers which are operated such that two ends of the lever arms pinch the bone therebetween. This allows the object to be attached to the bone without severely damaging the bone, like with bone screws.

Since time is a rare resource also in medical applications, it is desired that a bone clamp can easily and quickly be attached and/or released. This is achieved by the bone clamp of the present invention.

The bone clamp is defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The bone clamp comprises a first lever and a second lever which are connected to each other by a connection. The bone clamp further comprises a sliding block and a screw. The following notation is used in order to properly refer to the two levers: The first lever has a first lever arm from a first end of the first lever to the connection. It has a second lever arm from a second end of the first lever to the connection. The first end of the first lever is opposite to the second end of the first lever. The second lever has a third lever arm from a first end of the second lever to the connection and a fourth lever arm from a second end of the second lever to the connection. The second end of the second lever is opposite to the first end of the second lever.

The two levers are for example elongated. This means that the size of a lever in a principal direction is larger than the size in any other direction perpendicular thereto, for example by a factor like 2, 5 or 10. This principal direction then for example corresponds to the direction between the first and second ends of the lever.

The second ends of the two levers are to get in contact with the bone. For this purpose, the second ends of the two levers can optionally have a surface structure which improves the grip of the bone clamp on the bone. This surface might for example comprise spikes whose tips are to get in contact with the bone. Those tips might be tiltable relative to the respective lever, for example about one axis of rotation or two axes of rotation, wherein the two axes of rotation are for example perpendicular to each other. Tiltable spikes allow the bone clamp to better adapt to the surface of the bone to be clamped.

The sliding block is slidably attached to the first lever arm. This means that the sliding block can move along the first lever arm in a direction from the connection to the first end or vice versa.

The screw is pivotably mounted in the sliding block. This means that the screw can be turned about its longitudinal axis within the sliding block. The screw is held within the sliding block such that it cannot move along its longitudinal axis relative to the sliding block.

The first lever arm comprises a threaded surface for engaging with the screw mounted in the sliding block. So if the screw is turned, its thread rotates within the threaded surface of the first lever arm and thus causes a sliding movement of the sliding block along the first lever arm.

The longitudinal axis of the screw is for example parallel to the threaded surface. It is optionally further parallel or basically parallel to the direction from the first end of the first lever to the connection.

The sliding block comprises a sliding surface on which the third lever arm slides such that the second ends of the levers approach each other when the sliding block moves along the first lever arm in a predetermined direction. This predetermined direction is for example the direction from the first end of the first lever to the connection (the connection between the first and second levers).

So if the sliding block slides along the first lever arm in the predetermined direction, the contact between the sliding surface and the third lever arm urges the second ends of the levers towards each other, thus closing the bone clamp and exerting a clamping force on the bone.

In one embodiment, the first lever and the second lever basically extend parallel to each other. The connection is a pivot which allows a rotational movement between the two levers in one rotational dimension, for example in a rocker-like manner. The axis of rotation is for example perpendicular to a plane spanned by the two lever arms. In this configuration, the second ends of the two levers approach each other when the first ends of the two levers are moved away from each other. Further, in this configuration, the sliding surface of the sliding block pushes the third lever arm away from the first lever arm when it slides along the first lever arm in the predetermined direction, for example towards the pivot joint.

In another implementation of this embodiment, the connection is a sliding connection which allows a translational relative movement between the two levers in one translational dimension. This translational dimension for example occurs a direction which lies within a plane spanned by the two levers and being exactly or approximately orthogonal to the direction in which the levers extend, for example from their first ends to their second ends. In this configuration, the sliding surface of the sliding block acts, when the sliding block moves along the first lever arm in the predetermined direction, on the third lever arm such that the second lever is pulled towards the first lever. This results in the second ends of the two levers approaching each other.

In another embodiment, the two lever arms cross each other at the connection in a scissor-like manner. The connection is then a pivot joint with a pivot axis which is perpendicular to a plane spanned by the two levers. If the first ends of the two levers approach each other, then also the second ends of the two levers approach each other. In this configuration, the sliding surface of the sliding block pulls, when the sliding block slides along the first lever arm in the predetermined direction, the third lever arm towards the first lever arm, thus urging the second ends of the two levers towards each other.

In one embodiment, a play is provided between the first lever arm and the sliding block. This play does for example allow a movement of the sliding block relative to the first lever arm, for example in a direction orthogonal to the threaded surface of the first lever arm. With this relative movement, the thread of the screw partly or fully disengages from the threaded surface of the first lever arm, such that the sliding block can slide along the first lever arm without the need to turn the screw. This allows a fast sliding movement of the sliding block along the first lever arm, for example until the third lever arm gets into contact with the sliding surface and thereby urges the sliding block towards the first lever arm, whereby the thread of the screw engages the threaded surface of the first lever arm. By a subsequent operation of the screw, the sliding block can be further moved along the first lever arm in the predetermined direction, thus generating a clamping force.

In spinal applications, the bone clamp is typically applied from above, which means that the second ends of the two levers point towards the center of gravity of the earth. With the play between the first lever arm and the sliding block, the gravity can cause the thread of the screw to slide over the threaded surface of the first lever arm, thus disengaging the screw from the threaded surface. The sliding block then falls along the first lever arm in the predetermined direction until the sliding surface contacts the third lever arm. This enables a fast, automatic first part of the movement of the sliding block along the first lever arm, and the fine adjustment of the bone clamp can then be easily performed by operating the screw in the sliding block.

In one embodiment, the sliding surface of the sliding block has a convex curvature. This means that the distance of the sliding surface from the first lever arm increases with an increasing distance from the connection between the first and second levers. This means that the third lever arm is increasingly pushed away from the first lever arm with an ongoing movement of the sliding block along the first lever arm in the predetermined direction.

In one example, the convex curvature has a decreasing radius with an increasing distance from the connection between the levers. This optimizes the force exerted by the sliding block on the third lever arm over the movement of the sliding block along the first lever arm.

In one embodiment, the third lever arm has a curved sliding surface for sliding on the sliding surface of the sliding block. With the curvature of the sliding surface of the third lever arm, the clamping force of the bone clamp over the movement of the sliding block along the first lever arm can be controlled. This effect can even be enhanced in combination with a suitable curvature of the sliding surface of the sliding block.

In one embodiment, the third lever arm has an angled part at the second end of the second lever. The angled part is in particular angled away from the first lever arm. If the third lever arm contacts the first lever arm and the sliding block is far away from the connection between the two levers and moved towards this connection, the angled part of the second end of the second lever is pushed away from the first lever arm once the sliding block gets in contact with the third lever arm. This means that the third lever arm cannot block the movement of the sliding block along the first lever arm.

In one embodiment, the bone clamp further comprises biasing means for biasing the second ends of the levers towards each other. The biasing means for example involves a spring or an elastic element. For applying the bone clamp, the biasing force exerted by the biasing means has to be overcome, for example by operating the first lever arm and the third lever arm. This operation occurs as far away from the patient as possible, thus making the application of the bone clamp as easy as possible while maintaining a particular clamping force caused by the biasing means when there is no operation of the first and third lever arms.

In one embodiment, the bone clamp comprises a connector for connecting a marker device to the bone clamp. Via this connector, the marker device can be attached to the bone clamp, and thus to the bone, such that the bone can be tracked using a medical tracking system or medical navigation system.

In one embodiment, the marker connector comprises a first connector part, a second connector part and a union nut over the second connector part. The first connector part and the second connector part are to contact each other and the union nut is to maintain the contact between the first connector part and the second connector part.

The first and second connector parts and the union nut each have a longitudinal axis which coincide when the marker connector is in an assembled state. They then equal a longitudinal axis of the marker connector. It shall be noted that a longitudinal axis is virtual and not a mechanical element. The first and second connector parts are, in an assembled state of the marker connector, in contact with each other in the direction of the longitudinal axis.

The first connector part and the union nut each comprise at least one thread segment, the thread segments in the first connector part and the union nut for engaging each other. A thread segment of the first connector part consists, along the direction of the longitudinal axis of the first connector part, of at least two protrusions and an indentation between each pair of adjacent protrusions. A thread segment of the union nut consists, along the direction of the longitudinal axis of the union nut, of at least two protrusions and an indentation between each pair of adjacent protrusions. There are additional indentations in the first connector part and/or the second connector part such that every protrusion has a corresponding indentation.

In other words, the protrusions and indentations extend along the circumference of the first connector part and the union nut, respectively. They preferably have a thread pitch, such that a rotation of the union nut when the thread segments of the first connector part and the union nut engage with each other leads to a relative movement between the first connector part and the union nut along the longitudinal axis. One of the first connector parts and the union nut has its thread segment(s) on its inner circumference and the other one on its outer circumference. For example, the union nut has its thread segment(s) on its inner circumference and the first connector part has its thread segment(s) on its outer circumference.

Each thread segment extends only along a part of the circumference of the first connector part or the union nut, respectively. Each thread segment of the first connector part extends only along a part of the circumference of the first connector part and each thread segment of the union nut extends only along a part of the circumference of the union nut. This means that the union nut can be slid onto the first connector part, whereby the thread segments do not collide with each other, and the union nut can then be rotated relative to the first connector part about the longitudinal axis to tighten the connection between the first and second connector parts. The handling of the marker connector is thus similar to a bayonet lock.

In at least one of the first connector part and the union nut, at least one of the protrusions has a larger width in an axial direction (meaning the direction of the longitudinal axis) of the first connector part or the union nut, respectively, than the other protrusions. This can be understood in that the wider protrusion is thicker. The respective other one of the first connector part and the union nut has an indentation with a corresponding larger width (thickness) in an axial direction. The effect of this larger width protrusion/indentation pair is that the union nut can only be rotated relative to the first connector part in a particular axial alignment of the union nut and the first connector part. The union nut can for example only be turned if it is fully slid onto the first connector part.

In one embodiment, each segment of the first connector part and/or the union nut has a protrusion with a larger width. In one implementation, the protrusion with the larger width is the same protrusion in every thread segment.

In one embodiment, all thread segments of the first connector part are identical and/or all thread segments of the union nut are identical.

In one embodiment, the protrusion of a thread segment of the first connector part and/or the union nut closest to the respective other one of the first connector part and the union nut in the direction of the longitudinal axis of the first connector part or the union nut, in an assembled state of the marker connector, has the larger width. This means that the protrusions with the larger width pass by each other first when the union nut is slid onto the first connector part. If only the thread segment(s) of the first connector part has/have the larger width, then those larger width protrusions enter the union nut first when the marker connector is being assembled. This has the technical effect that the union nut can only be turned relative to the first connector part if it is slid far enough onto the first connector part such that the protrusion(s) with the larger width engage(s) (a) corresponding indentation(s).

In one embodiment, only the closest protrusion has the larger width.

In one embodiment, each thread segments extends along 45 degrees to 90 degrees of the circumference of the first connector part or the union nut, respectively. This leads to a large range of rotational angles between the union nut and the first connector part in which the thread segments of those elements engage each other. This in turn means a large possible corresponding axial movement between the union nut and the first connector part, which further depends on the thread pitch.

In one embodiment, the sum of the circumferential extends of the thread segments of the first connector part and the union nut is between 340 degrees and 360 degrees. This means that the union nut and the first connector part do not have to be exactly rotationally aligned before the union nut can be slid onto the first connector part.

The first connector part is for example a part of the first lever arm of the bone clamp. It can, however, be an integral part of any element of the bone clamp. Alternatively, it can be connected to any element of the bone clamp. The second connector part is a part of the marker device or can be connected to the marker device.

In one embodiment, the marker connector comprises a form fit between the first connector part and the second connector part, which allows only one of one or more rotational alignments between the first and second connector parts around the longitudinal axis in an assembled state of the marker connector. This means that the marker device can be connected to the bone clamp via the marker connector only in one out of a set of one or more relative positions defined by the one or more possible rotational alignments between the first and second connector parts.

The form fit is preferably designed such that there must be one of the one or more rotational alignments between the first and second connector parts in order for the thread segments of the first connector part and the union nut to be able to engage each other. So if there is another rotational alignment than one of the one or more possible rotational alignments, the second connector part cannot be attached to the first connector part via the union nut.

In one embodiment, the form fit involves one or more protrusions in the first connector part and at least the same number of corresponding indentations in the second connector part and/or one or more protrusions in the second connector part and at least the same number of corresponding indentations in the first connector part. Every protrusion must protrude into an indentation in order to achieve the form fit, thus enabling the threads of the first connector part and the union nut to engage with each other.

In one implementation, the number of indentations in one of the first connector part and the union nut is an integer multiple of the number of protrusions in the other one of the first connector part and the union nut. This is particularly useful if the protrusions and indentations are equally spaced and located on a circle which is centered about the longitudinal axis. However, any other distribution of protrusions and indentations can be implemented as long as only one or more rotational alignments between the first and second connector parts leads to every protrusion protruding into an indentation.

It shall be noted that the marker connector described herein can be understood as an invention in its own right. In addition, the marker connector is not limited to a connector for connecting a marker device to a bone clamp, but to connect any two objects. The first object comprises or is connected to the first connector part and the second object comprises or is connected to the second connector part.

Definitions

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual)

markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows to determine the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

BRIEF DESCRIPTION OF DRAWINGS

In the following, the invention is described with reference to the enclosed figures which represent preferred embodiments of the invention. The scope of the invention is not however limited to the specific features disclosed in the figures, which show.

DETAILED DESCRIPTION

Figure 1:
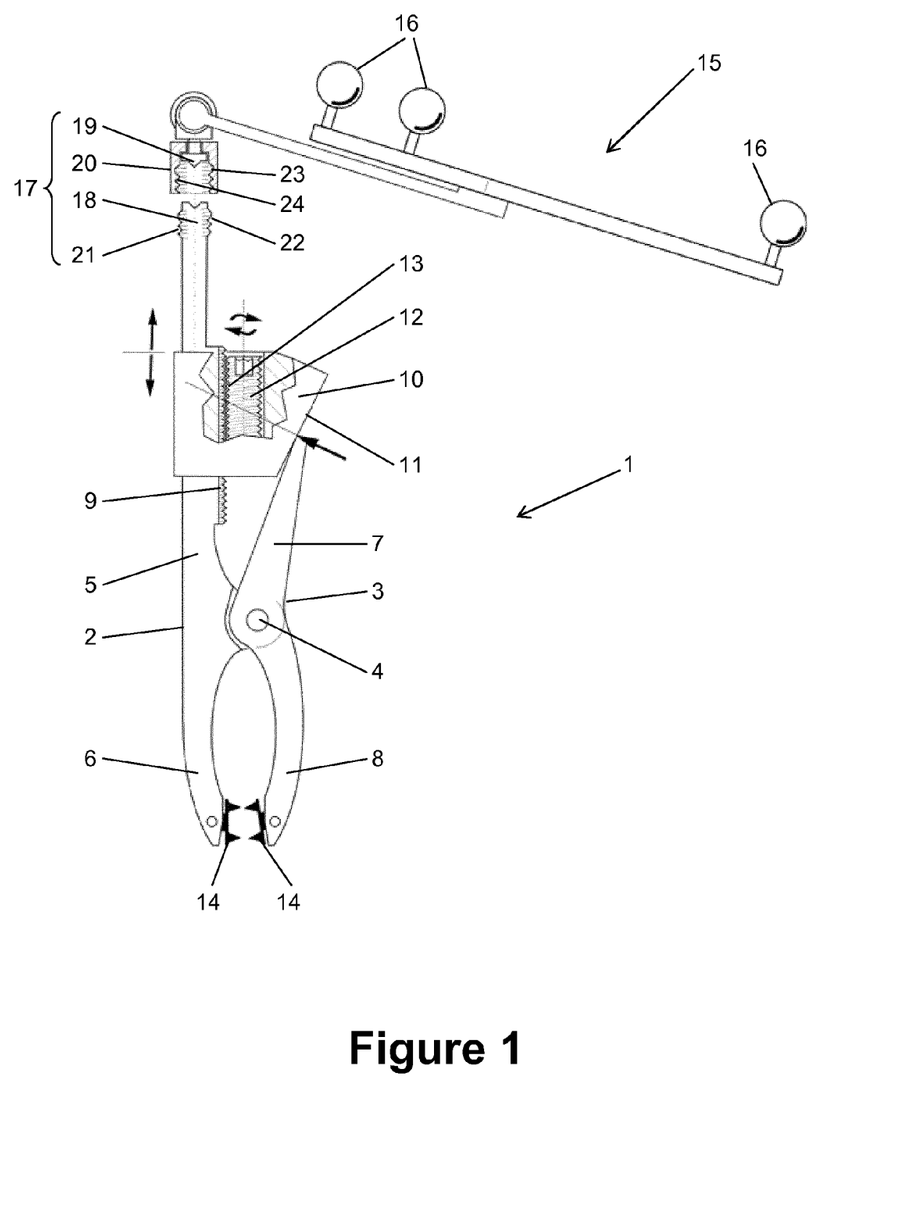
FIG. 1 a bone clamp.

FIG. 1 shows a partially sectional view of a bone clamp 1. The bone clamp 1 comprises a first lever 2 and a second lever 3 which are connected by a connection 4, which in the present embodiment is a pivot joint having one rotational degree of freedom. The two levers 2 and 3 extend basically parallel and do not cross each other at the connection 4.

Each lever arm 2 and 3 has a first end and a second end. In the position shown in FIG. 1, the first ends are the upper ends and the second ends are the lower ends. At the second ends, the two lever arms 2, 3 comprise spikes 14 which are to contact a bone to which the bone clamp 1 is to be attached. The spikes 14 are pivotably attached to the levers 2, 3, such that they can adapt to the surface of the bone.

The first lever 2 has a first lever arm 5 from the first end of the lever 2 to the connection 4 and a second lever arm 6 from the second end of the lever 2 to the connection 4. The second lever 3 has a third lever arm 7 from the first end of the lever 3 to the connection 4 and a fourth lever arm 8 from the second end of the lever 3 to the connection 4. On its side facing the third lever arm 7, the first lever arm 5 has a threaded surface 9.

A sliding block 10 is slidably attached to the first lever arm 5. In the viewing direction of FIG. 1, the sliding block 10 can move up and down along the first lever arm 5 as indicated by the straight arrows in FIG. 1.

A screw 12 is rotatably mounted in the sliding block 10. A part of the thread 13 of the screw 12 engages the threaded surface 9 of the first lever arm 5. A rotation of the screw 12 about its longitudinal axis as indicated by the curved arrows in FIG. 1, for example using a tool like a screwdriver, makes the screw 12 move along the threaded surface 9, thereby moving the sliding block 10 along the first lever arm 5. The screw 12 can preferably not move axially within the sliding block 10.

The sliding block 10 further comprises a sliding surface 11 for interacting with the third lever arm 7. The distance of the sliding surface 11 from the threaded surface 9 increases with increasing distance from the connection 4. So if the sliding block 10 moves towards the connection 4, which in the present embodiment is a movement in the predetermined direction, the third lever arm 7 is pushed away from the first lever arm 5, such that the second ends of the two levers 2, 3 approach each other. This means that the bone clamp 1 is closed, thus clamping the bone between the spikes 14.

In one embodiment, the shape of the third lever arm 7 and the sliding surface 11 of the sliding block 10 are designed such that the vector of the force exerted by the third lever arm 7 onto the sliding block 10 points through the screw 12 inside the sliding block 10, for example through a central part, such as the central third, of the screw 12. This avoids a tipping of the screw 12 within the sliding block 10, such that the screw 12 remains parallel or basically parallel to the threaded surface 9 of the first lever arm 5.

In the example shown in FIG. 1, the pivot joint by which the spikes 14 are connected to the second ends of the levers 2, 3 have one rotational degree of freedom. However, the joints could also have two rotational degrees of freedom, for example in terms of a ball-and-socket joint.

FIG. 1 further shows a marker device 15 which comprises a plurality of marker spheres 16 in a known spatial relationship. If the bone clamp is attached to a bone and the marker device 15 is attached to the bone clamp 1, the bone can be tracked by tracking the marker device 15.

The bone clamp 1 comprises a marker connector 17 for connecting the marker device 15 to the clamp 1. The marker connector 17 comprises a first connector part 18, a second connector part 19 and a union nut 20. The union nut 20 is put over the second connector part 19.

The first connector part 18 has two thread segments 21 and 22 and the union nut 20 has two thread segments 23 and 24, wherein the thread segments 21 to 24 of the first connector part 18 and the union nut 20 can engage with each other to lock the second connector part 19 to the first connector part 18.

The second connector part 19 is a part of the marker device 15 or is an element which can be attached to the marker device 15. The first connector part 18 is an extension of the first lever arm 5. Details of the marker connector 17 will be explained later.

Figure 2:
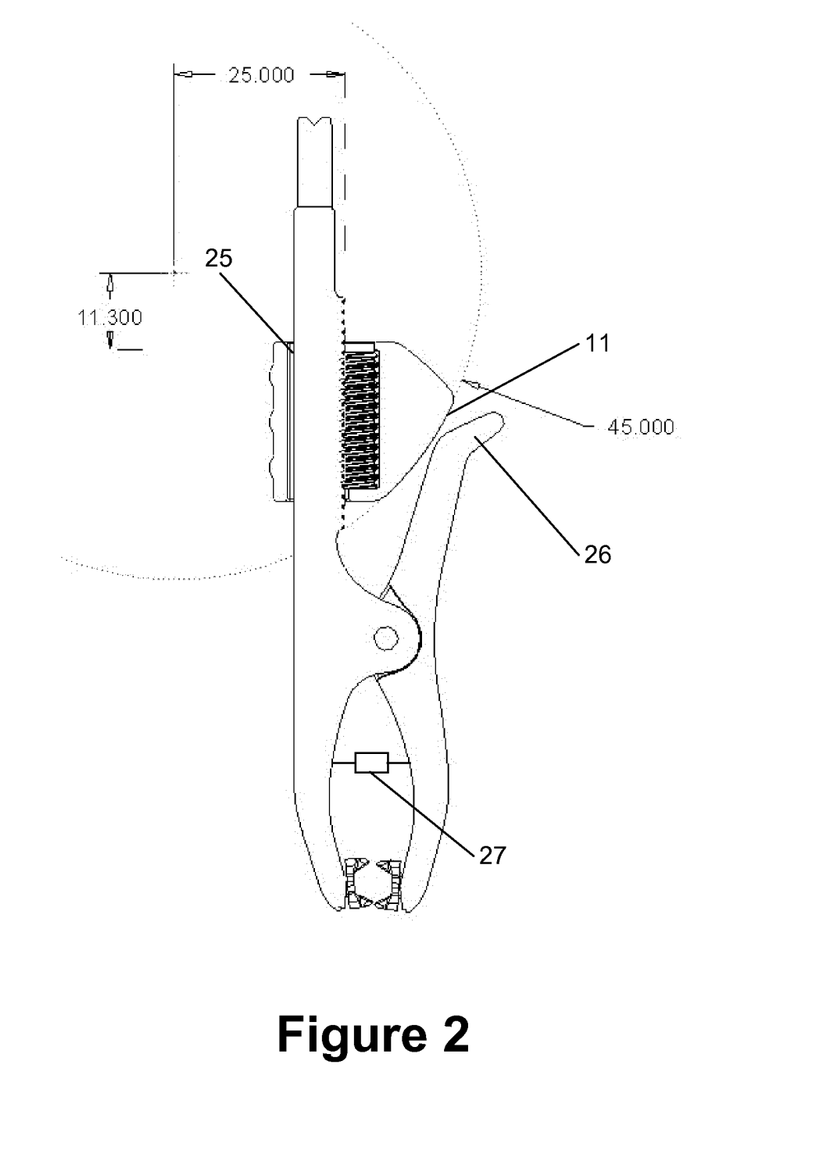
FIG. 2 a modified bone clamp.

FIG. 2 shows a partly sectional view of a modified version of the bone clamp 1. This modified version comprises a plurality of modifications which can be implemented separately or in any desired combination.

The first modification is a play 25 between the sliding block 10 and the first lever arm 5. This play can also be referred to as a gap. The play 25 enables the sliding block 10, and in particular the screw 12, to move away from the first lever arm 5 in a direction perpendicular to the threaded surface 9. This movement causes the thread 13 of the screw 12 to disengage from the threaded surface 9. In this case, the sliding block 10 can be moved along the first lever arm 5 without the need to turn the screw 12. This allows to quickly slide the sliding block 10, for example until the sliding surface 11 contacts the third lever arm 7. This sliding movement can for example be caused by gravity, in particular if the bone clamp 1 is used in an orientation as shown in FIG. 2 with the direction of gravity being downwards.

Once the sliding surface 11 is in contact with the third lever arm 7, this contact pushes the sliding block 10 towards the first lever arm 5, such that the thread 13 of the screw 12 re-engages with the threaded surface 9. From this point on, the screw 12 can again be turned in order to tighten the bone clamp 1 by further moving the sliding block 10 in the predetermined direction.

The second modification is an angled part 26 at the second end of the second lever 3. This angled part 26 can avoid jamming of the bone clamp 1.

In the example shown in FIG. 1, a situation can occur in which the sliding block 10 is far away from the connection 4 and the bone clamp 1 is fully open, such that the third lever arm 7 is in contact with the first lever arm 5. If the sliding block 10 is then moved towards the connection 4, its lower end pushes against the second end of the second lever 3, thus preventing the bone clamp from being closed. This situation cannot occur with the second modification using the angled part 26, because this angled part 26 glides over the sliding block 10 when it moves towards the connection 4 and thus pushes the third arm 7 away from the first lever arm 5. Other approaches for achieving this effect can be a suitable shape of the sliding block 10, in particular of the part facing towards the connection 4, or limiting the movement of the sliding block 10 in the opposite direction to the predetermined direction such that the side of the sliding block 10 which faces towards the connection 4 cannot get into contact with the first end of the second lever 3.

The third modification is the shape of the sliding surface 11. In the example of FIG. 1, the sliding surface 11 is straight. In the third modification, the sliding surface 11 of the sliding block 10 has a convex curvature, which for example means that the distance of the sliding surface 11 from the first lever arm 5 increases slower with an increasing distance from the connection 4. In the example shown in FIG. 2, the sliding surface 11 has the shape of a circular arc, with an exemplary radius of 45 mm.

The combination of the shape of the sliding surface 11 and the part of the third lever arm 7 which slides over the sliding surface 11 can be used to design the closing angle of the bone clamp 1 over the movement of the sliding block 10 along the first lever arm 5 and/or the direction of the vector of the force exerted by the third lever arm 7 on the sliding block 10.

The fourth modification is the presence of biasing means 27, such as a spring. The biasing means 27 exerts a force on the levers 2, 3 that closes the bone clamp 1.

Figure 3:
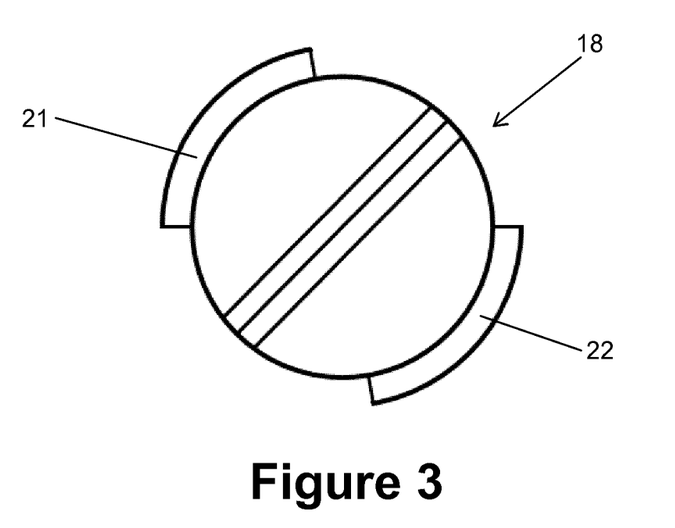
FIG. 3 an axial view of a first connector part.
Figure 4:
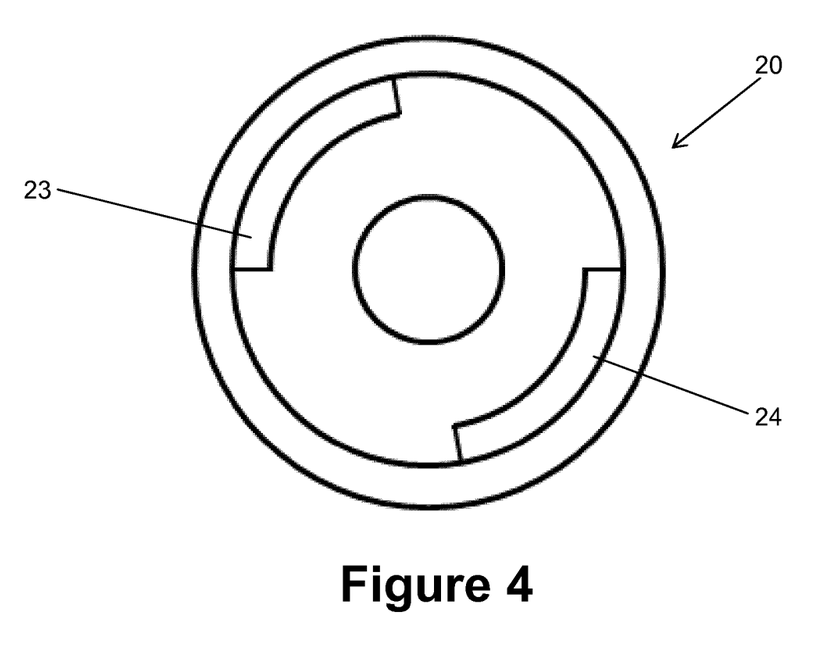
FIG. 4 an axial view into a union nut.

Details of the marker connector 17 are shown in FIGS. 3 and 4 in addition to FIG. 1. In FIG. 1, axial directions in terms of longitudinal axes of the first connector part 18, the second connector part 19 and the union nut 20 extend in an up-down direction. When the marker connector 17 is assembled, the longitudinal axes coincide.

FIG. 3 shows an axial view onto the first connector part 18 (from above in FIG. 1) and FIG. 4 shows an axial view into the union nut 20 (from below in FIG. 1).

As can be seen from FIG. 3, the two thread segments 21 and 22 of the first connector part 18 each extend along 85 degrees of the outer circumference of the first connector part 18 and are opposite to each other. As can be seen from FIG. 4, the two thread segments 23 and 24 of the union nut 20 each extend along 85 degrees of the inner circumference of the union nut 20 and are opposite to each other. This means that the union nut 20 can be slid onto the first connector part 18 in an axial direction if the first connector part 18 and the union nut 20 are rotationally aligned correctly. The thread segments 21 to 24 then slide past each other. If the union nut 20 is fully slid onto the first connector part 18, the union nut 20 can be turned relative to the first connector part 18 such that the thread segments 21 and 22 of the first connector part 18 and the thread segments 23 and 24 of the union nut 20 engage with each other, thus urging the second connector part 19 towards the first connector part 18.

The union nut 20 has a collar at its side which is facing away from the first connector part 18 and can contact a surface of the second connector part 19 which is also facing away from the first connector part. This collar can thus push the second connector part 19 towards the first connector part 18.

As can be seen from FIG. 1, the thread segments 21 and 22 of the first connector part 18 consist of alternating protrusions and indentations in an axial direction and have a thread pitch in the axial direction. In the present example, each thread segment 21, 22 has three protrusions. The thread segments 23 and 24 of the union nut 20 have corresponding protrusions and indentations for accommodating the thread segments 21 and 22 of the first connector part 18.

As can be further seen from FIG. 1, the protrusions within a thread segment 21 and 22, respectively, have different widths in the axial direction. In the present example, the protrusion closest to the second connector part 19 in an assembled state of the marker connector 17 has a width which is larger than the width of the other protrusions.

Since the thread segments 23 and 24 of the union nut 20 have a shape inverse to the shape of the thread segments 21 and 22 of the first connector part 18, the union nut 20 cannot be turned relative to the first connector part 18 about the longitudinal axis if it is not fully slid onto the first connector part 18, because the wider protrusions of the thread segments 21 and 22 have no mating indentations in the thread segments 23 and 24. This means that the marker connector 17 can only be locked if it is correctly assembled.

As can further be seen from FIGS. 1 and 3, the first connector part 18 has a V-shaped groove at its front face facing the second connector part 19. This V-shaped groove connects diametral points on the front face of the first connector part 18. The second connector part 19 has a corresponding protrusion for mating with the V-shaped groove in the first connector part. This means that the protrusion of the second connector part 19 can only extend into the V-shaped groove of the first connector part 18 in one of two rotational alignments of the first connector part 18 and the second connector part 19 about the longitudinal axis. Only in one of those two alignments, the first connector part 18 and the second connector part 19 can be close enough to each other such that the wider protrusions of the thread segments 21 and 22 can engage with corresponding indentations of the thread segments 23 and 24. The marker connector 17 can therefore only be locked if the second connector part 19 is correctly aligned with the first connector part 18.

The engagement of the V-shaped groove in the first connector part 18 and the protrusion of the second connector part 19 further ensures that the second connector part 19 cannot rotate relative to the first connector part 18 once the marker connector 17 is locked.

In this context, the term "locked" means that the union nut 20 is rotated about the longitudinal axis relative to the first connector part 18 such that the second connector part 19 is pushed against the first connector part with a predetermined force, which is for example sufficient to maintain the alignment between the first connector part 18 and the second connector part 19.

The invention claimed is:

1. A bone clamp for attachment to a bone, the bone clamp comprising a first lever and a second lever that are rotatably connected to each other at a connection, a sliding block, and a screw, wherein:
   the first lever and the second lever are rotatable relative to each other about the connection;
   the first lever has a first lever arm from a first end of the first lever to the connection and a second lever arm from a second end of the first lever opposite to the first end to the connection,
   the second lever has a third lever arm from a first end of the second lever to the connection and a fourth lever arm from a second end of the second lever opposite to the first end to the connection,
   the second ends of the two levers are configured to contact the bone,
   the sliding block is slidably attached to the first lever arm,
   the screw is pivotably mounted in the sliding block,
   the first lever arm comprises a threaded surface for engaging with the screw mounted in the sliding block, and
   the sliding block comprises a sliding surface on which the third lever arm slides such that the second ends of the levers approach each other when the sliding block moves along the first lever arm in a predetermined direction.

2. The bone clamp of claim 1, wherein a play is provided between the first lever arm and the sliding block.

3. The bone clamp of claim 1, wherein the sliding surface of the sliding block has a convex curvature.

4. The bone clamp of claim 3, wherein the convex curvature has a decreasing radius with an increasing distance from the connection between the levers.

5. The bone clamp of claim 1, wherein the third lever arm has a curved sliding surface for sliding on the sliding block.

6. The bone clamp of claim 1, wherein the third lever arm has an angled part at the second end of the second lever.

7. The bone clamp of claim 1, further comprising biasing means for biasing the second ends of the levers towards each other.

8. The bone clamp of claim 1, further comprising a marker connector for connecting a marker device to the bone clamp.

9. The bone clamp of claim 8, wherein the marker connector comprises a first connector part, a second connector part, and a union nut over the second connector part, wherein:
   the first and second connector parts and the union nut each have a longitudinal axis that coincide when the marker connector is in an assembled state,
   the first connector part and the union nut each comprise at least one thread segment, the thread segments in the first connector part and the union nut for engaging each other,
   the at least one thread segment of the first connector part consists, along the direction of the longitudinal axis of the first connector part, of at least two protrusions and an indentation between each pair of adjacent protrusions,
   the at least one thread segment of the union nut consists, along the direction of the longitudinal axis of the union nut, of at least two protrusions and an indentation between each pair of adjacent protrusions,
   each thread segment extends only along a part of a circumference of the first connector part or the union nut, respectively, and
   in at least one of the first connector part and the union nut, at least one of the protrusions has a larger width in an axial direction of the first connector part or the union nut, respectively, than the other protrusions.

10. The bone clamp of claim 9, wherein the protrusion of a thread segment of the first connector part and/or the union nut closest to the respective other one of the first connector part and the union nut in the direction of the longitudinal axis of the first connector part or the union nut, in an assembled state of the marker connector, has the larger width.

11. The bone clamp of claim 10, wherein only the closest protrusion has the larger width.

12. The bone clamp of claim 9, wherein each thread segment extends along 45 degrees to 90 degrees of the circumference of the first connector part or the union nut, respectively.

13. The bone clamp of claim 9, wherein the sum of circumferential extents of the thread segments of the first connector part and the union nut is between 340 degrees and 360 degrees.

14. The bone clamp of claim 9, further comprising a form fit between the first connector part and the second connector part that allows only one of one or more rotational alignments between the first and second connector parts around the longitudinal axis in an assembled state of the marker connector.

15. The bone clamp of claim 14, wherein the form fit involves one or more protrusions in the first connector part and at least the same number of corresponding indentations in the second connector part and/or one or more protrusions in the second connector part and at least the same number of corresponding indentations in the first connector part.

16. The bone clamp of claim 1, wherein the screw is pivotably mounted in the sliding block such that the screw is turnable about a longitudinal axis of the screw and cannot move along the longitudinal axis relative to the sliding block.

17. The bone clamp of claim 16, wherein the screw is turnable such that a thread on the screw rotates within the threaded surface of the first lever arm thereby causing a sliding movement of the sliding block along the first lever arm.

18. A bone clamp attachable to a bone, the bone clamp comprising:
   a first lever having first and second ends and a threaded surface, wherein the second end is configured to contact the bone;
   a second lever having first and second ends, wherein the second end is configured to contact the bone;
   a connection connecting the first lever and the second lever, the first lever and the second lever being rotatable relative to each other about the connection;
   a sliding block slidably attached to the first lever and including a sliding surface on which the second lever slides such that the second ends of the first and second levers approach each other when the sliding block moves in a first direction from the first end of the first lever towards the second end; and a screw pivotably mounted in the sliding block and configured to engage the threaded surface of the first lever.

19. The bone clamp of claim 18, wherein play is provided between the first lever and the sliding block such that the screw does not engage the threaded surface of the first lever when the clamp is in an unclamped position.

20. The bone clamp of claim 19, wherein when the clamp is in a clamped position, the second lever is configured to push the sliding block such that the screw engages the threaded surface.

* * * * *